United States Patent [19]

Sakata et al.

[11] Patent Number: 5,384,248
[45] Date of Patent: Jan. 24, 1995

[54] PROCESS FOR MEASURING AN ANALYTE WITH AN OXIDASE AND AN OXIDIZABLE COLOR REAGENT AND SURFACTANTS

[75] Inventors: Yoshitsugu Sakata, Otsu; Toshiro Hanada, Amagasaki; Ryosuke Matsuda, Osaka; Yoshiyuki Matsuda, Ibaraki, all of Japan

[73] Assignee: Wako Pure Chemical Industries, Ltd., Osaka, Japan

[21] Appl. No.: 228,002

[22] Filed: Apr. 15, 1994

Related U.S. Application Data

[63] Continuation of Ser. No. 921,958, Jul. 31, 1992, abandoned, which is a continuation of Ser. No. 533,558, Jun. 5, 1990, abandoned.

[30] Foreign Application Priority Data

Jun. 9, 1989 [JP] Japan ................ 1-147000

[51] Int. Cl.⁶ ............... C12Q 1/46; C12Q 1/36; C12Q 1/62; C12Q 1/60
[52] U.S. Cl. ................... 435/25; 435/20; 435/10; 435/11
[58] Field of Search .......... 435/20, 25, 10, 11

[56] References Cited

U.S. PATENT DOCUMENTS

| | | | |
|---|---|---|---|
| 3,754,865 | 8/1973 | Gindler | 436/17 |
| 4,485,176 | 11/1984 | Bollin et al. | 436/86 |
| 4,547,460 | 10/1985 | Eikenberry | 436/170 |
| 4,673,635 | 6/1987 | Yamanishi et al. | 436/904 |
| 4,737,457 | 4/1988 | Evans et al. | 436/904 |

FOREIGN PATENT DOCUMENTS

| | | |
|---|---|---|
| 0072450 | 2/1983 | European Pat. Off. . |
| 0351772 | 1/1990 | European Pat. Off. . |

OTHER PUBLICATIONS

Patent Abstracts of Japan, vol. 9, No. 5 (C-260)[1728], 10th Jan. 1985; & JP-A-59 159 798 (Amano Seiyaku K.K.) Sep. 10, 1984.

Patent Abstracts of Japan, vol. 10, No. 12 (P-421)[2069], 17th Jan. 1986; & JP-A-60 168 050 (Wako Junyaku Kogyo K.K.) Aug. 31, 1985.

*Primary Examiner*—Douglas W. Robinson
*Assistant Examiner*—Jon P. Weber
*Attorney, Agent, or Firm*—Armstrong, Westerman, Hattori, McLeland & Naughton

[57] ABSTRACT

A substrate or an enzymatic activity in a body fluid can be measured accurately without influences of interfering substances such as bilirubin by reacting an oxidase corresponding to an analyte with the analyte or an oxidase corresponding to a substance produced by enzymatic reaction with the substance in a measuring system containing one or more cationic and/or amphoteric surfactants, followed by optical measurement of hydrogen peroxide produced by the reaction.

21 Claims, No Drawings

PROCESS FOR MEASURING AN ANALYTE WITH AN OXIDASE AND AN OXIDIZABLE COLOR REAGENT AND SURFACTANTS

This application is a continuation of application Ser. No. 07/921,958 filed Jul. 31, 1992, now abandoned, which is a continuation of application Ser. No. 07/533,558 filed Jun. 5, 1990, now abandoned.

BACKGROUND OF THE INVENTION

The present invention relates to a process for measuring a body fluid component by an enzymatic method using an oxidizable color reagent. More particularly, it relates to a process for measuring a substrate or an enzymatic activity by an enzymatic method using an oxidiazable color reagent which process is free from influences of interfering substances such as bilirubin and hemoglobin which are present in body fluids.

Measurement of living body components, for example, body fluid .components such as blood and urine is indispensable for diagnoses of diseases, elucidation of pathosis, and judgement of progress towards recovery because the change of amounts of the living body components is closely related to diseases. There have been developed methods for measurement of great many body fluid components such as cholesterol, uric acid, glucose, triglycerides, phospholipids, choline, creatine, creatinine, bile acid, monoamine oxidase, etc. It is generally known that these methods are useful for diagnoses of diseases.

As methods for measurement of serum components, so-called "enzymatic methods" have been generalized. In the enzymatic methods, when an objective component is other than enzymes, there is used an enzyme which acts specifically on the objective component. When an objective component is an enzyme, there is used a compound which is a substrate for the enzyme. In each of these cases, enzymatic reaction is carried out and the reaction product is measured, whereby the amount of objective component is determined. Of the enzymatic methods, there are being increased, with development of oxidizable color reagents, methods which comprise acting a hydrogen peroxide producing enzyme, for example, an oxidase, on an objective component or a substance derived therefrom, to produce hydrogen peroxide in an amount corresponding to the amount of the objective component or substance derived therefrom, introducing the hydrogen peroxide into a color-producing system using peroxidase and an oxidizable color reagent as color-producing component, carrying out calorimetric determination on the basis of the coloration thus caused, and thereby determining the amount of the objective component. An example of such method is a method which comprises introducing hydrogen peroxide produced by a combination of cholesterol and cholesterol oxidase; a triglyceride, lipoprotein lipase and glycerol oxidase; uric acid and uricase; or the like into a color-producing system using peroxidase and an oxidizable color reagent, measuring absorbance due to the coloration thus caused, and thereby determining the amount of an objective component.

However, these methods for measuring a body fluid component by an enzymatic method using an oxidizable color reagent tend to be affected by the reducing action of reductive substances which are present in a sample, for example, ascorbic acid, bilirubin, hemoglobin, etc., and therefore negative errors often took place in measured values. Pigments such as hemoglobin and bilirubin cause errors in measurement, depending on measuring wavelength. Moreover, as generally known, absorption due to these pigments themselves varies with the lapse of time during measurement, depending on light, components in reagents, etc. and affects measurement results. Therefore, for removing these interfering substances, various methods have been proposed and investigated.

As methods for decomposing ascorbic acid among the interfering substances, there have been disclosed, for example, a method using ascorbate oxidase (Japanese Patent Publication No. 56-39198), a method using iodic acid or a salt thereof, or periodic acid or a salt thereof (Japanese Patent Appln. Kokai (Laid-Open) Nos. 56-109595, 56-151358 and 56-107161), and a method using copper ions (Japanese Patent Appln. Kokai (Laid-Open) No. 60-262599). Of these methods, the method using ascorbate oxidase in which reaction can be carried out under mild conditions is the most widespread. Since ascorbate oxidase is an enzyme, this method involves an inherent problem, i.e., insufficient heat stability and storage stability, but there has been constituted a measuring system which is hardly affected by ascorbic acid in practice. Therefore, there is a relatively slight desire to seek further improvement in this method. On the other hand, as methods for avoiding the influence of bilirubin, there have been disclosed, for example, a method using copper ions (Japanese Patent Appln. Kokai (Laid-Open) No. 60-262599), a method using a ferrocyanide (Clin. Chem. 26 (20), 227 (1980)), and a method using bilirubin oxidase. These methods involve problems such as insufficient storage stability of reagents, inhibition of an enzyme used in a measuring system and the like, etc., and a satisfactory method has not yet been established. As a method for avoiding the influence of hemoglobin, there has been disclosed, for example, a method using thiourea (Japanese Patent Appln. Kokai (Laid-Open) No. 62-248500). Since thiourea is a strong reducing agent, this method is too disadvantageous to be applied to a measuring system utilizing a redox reaction.

SUMMARY OF THE INVENTION

The present invention was made in consideration of such conditions and is intended to provide a method for avoiding influences of bilirubin and hemoglobin in measurement of a body fluid component by an enzymatic method using an oxidizable color reagent, and a process for measuring a body fluid component which process is free from influences of these interfering substances.

The present invention provides a process for measuring a substrate or an enzymatic activity in a body fluid which comprises acting an oxidase corresponding to an analyte to be measured on the analyte, or acting an oxidase corresponding to a substance produced by enzymatic reaction on the substance, in a measuring system, and measuring hydrogen peroxide produced, optically by use of an oxidizable color reagent, said measuring system comprising at least one member selected from the group consisting of cationic surfactants and amphoteric surfactants in order to avoid influences of measurement-interfering substances present in the body fluid.

DESCRIPTION OF THE PREFERRED EMBODIMENTS

In order to avoid influences of bilirubin and hemoglobin both present in a body fluid in a process for measuring a body fluid component by an enzymatic method using an oxidizable color reagent, the present inventors earnestly investigated and consequently found that this purpose can be achieved by placing at least one cationic surfactant and/or at least one amphoteric surfactant in a measuring system, whereby the present invention was accomplished. Here, the process for measuring a body fluid component by an enzymatic method using an oxidizable color reagent is a method which comprises acting an oxidase on an objective component or a substance derived therefrom, to produce hydrogen peroxide in an amount corresponding to the amount of the objective component or substance derived therefrom, introducing the hydrogen peroxide into a color-producing system using peroxidase and an oxidizable color reagent, carrying out calorimetric determination on the basis of the coloration thus caused, and thereby determining the amount of the objective body fluid component.

As the cationic surfactant and/or amphoteric surfactant used in this invention, any cationic surfactant or amphoteric surfactant, or both, may be used so long as the object of this invention can be achieved. Typical examples of the cationic surfactant are compounds of the following general formulas [I] to [VII]:

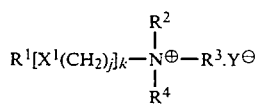   [I]

wherein $R^1$ and $R^2$ are independently a hydrogen atom, a linear or branched, saturated or unsaturated alkyl group having 1 to 22 carbon atoms, a phenyl group a substituted phenyl group (the substituent is a linear or branched alkyl group having 1 to 12 carbon atoms, an alkoxy group having 1 to 5 carbon atoms, or a halogen atom), an aralkyl group (e.g. benzyl group or phenethyl group), a substituted aralkyl group (the substituent is a linear or branched alkyl group having 1 to 12 carbon atoms, an alkoxy group having 1 to 5 carbon atoms, or a halogen atom), or a cycloalkyl group having 5 or 6 carbon atoms, one of the hydrogen atoms of each of the functional groups from the alkyl group to the cycloalkyl group being able to be replaced by a hydroxyl group or an amino group; $R^3$ and $R^4$ are independently a hydrogen atom, a linear or branched alkyl group having 1 to 4 carbon atoms, a phenyl group or a tolyl group, one of the hydrogen atoms of each of the functional groups from the alkyl group to tolyl group being able to be replaced by a hydroxyl group or an amino group; $X^1$ is an oxygen atom, a sulfur atom, —N(CH$_3$)—, —CO—, —CONH—, —NHCO—, —COO—, —OCO—, —SO$_2$NH—, —NHSO$_2$—, —SO$_3$—, —OSO$_2$—, or —OSO$_3$—; Y is a univalent anion (e.g. an anion of a halogen atom such as chlorine, bromine or iodine, or a conjugate base of acetic acid, lactic acid, sulfuric acid, monomethylsulfuric acid or the like); j is an integer of 1 to 3; k is an integer of 0 to 25; there are excepted the case where all of $R^1$, $R^2$, $R^3$ and $R^4$ are hydrogen atoms and k is zero, and the case where $X^1$ is —CO—, —CONH—, —COO—, —SO$_2$NH—, —SO$_3$— or —OSO$_2$— and $R^1$ is a hydrogen atom.

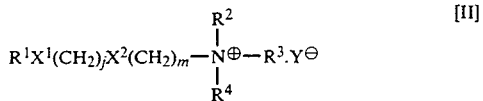   [II]

wherein $X^2$ is an oxygen atom, a sulfur atom, —N(CH$_3$)—, —CO—, —CONH—, —NHCO—, —COO—, —OCO—, —SO$_2$NH—, —NHSO$_2$—, —SO$_3$—, —OSO$_2$— or —OSO$_3$—; m is an integer of 1 to 3; $R^1$, $R^2$, $R^3$, $R^4$, $X^1$, Y and j are as defined above; there is excepted the case where $X^1$ is —CO—, —CONH—, —COO—, —SO$_2$NH—, —SO$_3$— or —OSO$_2$— and $R^1$ is a hydrogen atom.

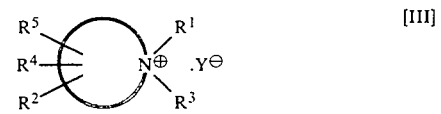   [III]

wherein

is a 5- or 6-membered saturated heterocyclic ring containing the nitrogen atom or a condensed ring formed therefrom; $R^5$ is a hydrogen atom, a linear or branched alkyl group having 1 to 4 carbon atoms, a phenyl group or a tolyl group, one of the hydrogen atoms of each of the functional groups from the alkyl group to tolyl group being able to be replaced by a hydroxyl group or an amino group; and $R^1$, $R^2$, $R^3$ and $R^4$ and Y are as defined above.

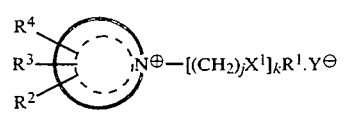   [IV]

wherein

is a 5- or 6-membered unsaturated heterocyclic ring containing the nitrogen atom, or a condensed ring formed therefrom; and $R^1$, $R^2$, $R^3$, $R^4$, $X^1$, Y, j and k are as defined above.

   [V]

wherein $R^1$, $R^2$, $R^3$, $R^4$ and Y are as defined above; there is excepted the case where one or more members out of $R^1$, $R^2$, $R^3$ and $R^4$ are hydrogen atoms.

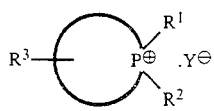 [VI]

wherein

is a 5- or 6-membered saturated heterocyclic ring containing the phosphorus atom; $R^1$, $R^2$, $R^3$ and Y are as defined above; there is excepted the case where R1 or $R^2$, or both, are hydrogen atoms.

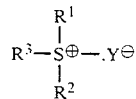 [VII]

wherein $R^1$, $R^2$, $R^3$, and Y are as defined above; there is excepted the case where one or more members out of $R^1$, $R^2$ and $R^3$ are hydrogen atoms.

Typical examples of the amphoteric surfactant are compounds of the following general formulas [VIII] to [XII]:

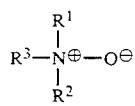 [VIII]

herein $R^1$, $R^2$, and $R^3$ are as defined above; there is excepted the case where one or more members out of $R^1$, $R^2$ and $R^3$ are hydrogen atoms.

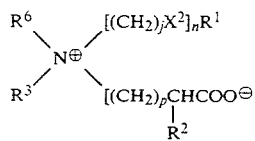 [IX]

wherein $R^6$ is a hydrogen atom, a linear or branched, saturated or unsaturated alkyl group having 1 to 22 carbon atoms, a phenyl group, a substituted phenyl group (the substituent is a linear or branched alkyl group having 1 to 12 carbon atoms, an alkoxy group having 1 to 5 carbon atoms, or a halogen atom), an aralkyl group (e.g. benzyl group or phenethyl group), a substitued aralkyl group (the substitutent is a linear or branched alkyl group having 1 to 12 carbon atoms, an alkoxy group having 1 to 5 carbon atoms, or a halogen atom), or a cycloalkyl group having 5 or 6 carbon atoms, one of the hydrogen atoms of each of the functional groups from the alkyl group to the cycloalkyl group being able to be replaced by a hydroxyl group or an amino group; n and p are independently zero or an integer of 1 to 3; and $R^1$, $R^2$, $R^3$, $X^2$ and j are as defined above.

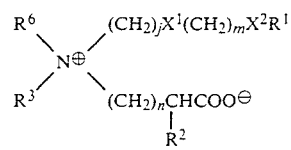 [X]

wherein $R^1$, $R^2$, $R^3$, $R^6$, $X^1$, $X^2$, j, m and n are as defined above.

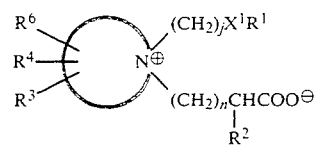 [XI]

wherein

is a 5- or 6-membered saturated heterocyclic ring containing the nitrogen atom, or a condensed ring formed therefrom; and $R^1$, $R^2$, $R^3$, $R^4$, $R^6$, $X^1$, j and n are as defined above.

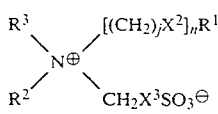 [XII]

where $X^3$ is a lower alkylene group or a phenylene group; and $R^1$, $R^2$, $R^3$, $X^2$, j and n are as defined above.

Specific examples of compound of the general formula [I] are hydrochlorides, acetates, lactates and the like of primary to tertiary amines such as laurylamine, stearylamine, laurylstearylamine, [2-(palmitylcarbonyloxy)ethyl]dimethylamine, (polyoxyethylene)-laurylamine, laurylmethylaniline, etc.; and quaternary ammonium salts such as cetyltrimethylammonium bromide, myristyltrimethylammonium bromide, benzyldecyldimethylammonium chloride, (4-lauryl-2-methylbenzyl)trimethylammonium chloride, lauryldimethyl[2-(4-t-octylphenyl)ethyl]ammonium bromide, (laurylthiomethyl)trimethylammonium chloride, benzyldiethyl-[2-(palmitylcarbonylamino)ethyl]ammonium chloride, benzyldimethyl-[3-(isopropylsulfonylamino)propyl]ammonium chloride, 2-(decylmethylamino)ethyltrimethylammonium bromide, benzyldimethyl[(4-t-octylphenyl)polyoxyethylene]ammonium chloride, etc. Specific examples of compound of the general formula [II] are bis(hydroxyethyl)-(stearoylaminomethylcarbonyloxy)ethylamine hydrochloride, (lauroyloxyethylaminocarbonyl)methyltrimethylammonium chloride, [2-(4-t-octylphenoxy)ethoxy]methyltrimethylammonium iodide, etc. Specific examples of compound of the general formula [III] are 2-[(4-t-octylphenoxy)ethoxy]ethylmorpholine hydrochloride, benzyl-2-[(4-t-octylphenoxy)ethoxy]ethylpiperadinium chloride, 2-heptadecyl-4-isopropyl-4,5-dihydroimidazole hydrochloride, 1-benzyl-1-hydroxyethyl-2-tridecyl-4,5-dihydroimidazolium chloride, etc. Specific examples of compound of the general formula [IV] are laurylpyridinium chloride, laurylisoquinolinium chloride, palmityloxymethylpyridinium chloride, 2,3-diphenyl-5-undecyltetrazolium chloride, etc. Specific examples of compound of the general formula [V] are lauryltrimethylphosphonium bromide, lauryl(tri-p-tolyl)-phosphonium chloride, etc. Specific examples of compound of the general formula [VI] are laurylphenylcyclotetramethylenephosphonium bromide, etc. Specific examples of compound of the general formula [VII] are benzyllaurylmethylsulfonium methylsulfate, ethylpalmitylmethylsulfonium methylsulfate, etc. Specific examples of compound of the general formula [VIII] are lauryldimethylamine oxide, etc. Specific examples of compound of the general formula [IX] are N,N-bis(octylaminoethyl)glycine, N-laurylalanine, lauryl-N,N,N-trimethyl-a-betaine, N-stearyloxymethyl-N,N-dimethylbetaine, N-laurylthiomethyl-N,N-dimethylbetaine, etc. Specific examples of compound of the general formula [X] are N-(laurylthioethoxy)methyl-N,N-dimethylbetaine, etc. Specific examples of compound of the general formula [XI] are N-carboxymethyl-N-(stearyloxymethyl)piperidiniumbetaine, 2-lauryl-1-carboxymethyl-1-(2-hydroxyethyl)imidazoliumbetaine, etc. Specific examples of compound of the general formula [XII] are N-palmitylsulfotaurine, 4-(palmitylaminomethyl)-benzenesulfonic acid, etc. However, needless to say, these specific examples are merely by way of illustration and the cationic and amphoteric surfactants according to this invention are not limited thereto. The above-exemplified cationic or amphoteric surfactants, or both, are used usually in a concentration of 0.001 to 10%, preferably 0.01 to 3%, in a sample, and may be used singly or in combination of two or more thereof. In addition, there may be co-used substances which have heretofore been used for avoiding influences of interfering substances, for example, copper ions, ferrocyanides, etc., which are used for avoiding influences of bilirubin.

Body fluid components measurable by the process of this invention include, for example, substrates such as cholesterol, uric acid, glucose, triglycerides, phospholipids, choline, creatine, creatinine, bile acid, lactic acid, free fatty acids, pyruvic acid, etc.; and enzymes such as monoamine oxidase, guanase, choline esterase, etc. The body fluid components are not particularly limited thereto, and the process of this invention permits measurement of all body fluid components which can be measured by determining quantitatively hydrogen peroxide produced by enzymatic reaction.

It is sufficient that the measuring process of this invention is practiced according to a process for measuring a body fluid component by a per se well-known enzymatic method using an oxidizable color reagent (in which the amount of an objective body fluid component is determined by measuring hydrogen peroxide produced by enzymatic reaction, optically by use of an oxidizable color reagent), except that at least one cationic surfactant or at least one amphoteric surfactant, or both, are placed in a measuring system (usually by addition to a liquid reagent) in order to avoid influences of measurement-interfering substances present in body fluids.

In determining a body fluid component quantitatively by the process of this invention, the kinds and the using amounts of the oxidase used as an enzyme for producing hydrogen peroxide, other enzymes used for other purposes, a substrate which participates in the enzymatic reaction, and other substances may be properly chosen depending on an analyte to be measured, in accordance with a per se well-known process for measuring a body fluid component by use of an oxidizable color reagent.

As the oxidizable color reagent used in the measuring process of this invention, any one may be used so long as it reacts with hydrogen peroxide to develop a color. The oxidizable color reagent include, for example, a combination of 4-aminoantipyrine and a phenolic compound, a naphthal compound or an aniline compound; a combination of 3-methyl-2-benzothiazolinonehydrazone and an aniline compound; 2,2'-azino-bis(3-ethylbenzothiazoline-6-sulfonic acid); triphenylmethane series leuco dyes; diphenylamine derivatives; benzidine derivatives; triarylimidazole derivatives; Leucomethylene Blue derivatives; o-phenylenediamine derivatives; etc. Specific examples of the phenolic compound used in combination with 4-aminoantipyrine are phenol, p-chlorophenol, 2,4-dichlorophenol, etc. Specific examples of the naphthol compound used in combination with 4-aminoantipyrine are 1-naphthol, 1-naphthol-2-sulfonic acid, 1-naphthol-2-carboxylic acid, etc. Specific examples of the aniline compound used in combination with 4-aminoantipyrine or 3-methyl-2-benzothiazolinonehydrazone are aniline, N,N-diethylaniline, N-ethyl-N-($\beta$-hydroxyethyl-m-toluidine, N-ethyl-N-(2-hydroxy-3-sulfopropyl-)-3,5-dimethoxyaniline, N-ethyl-N-(2-hydroxy-3-sulfopropyl)-m-toluidine, etc. Specific examples of the triphenylmethane series leuco dyes are leuco-malachite green, bis(p-diethylaminophenyl)-2-sulfophenylmethane, bis(p-diethylaminophenyl)-3,4-disulfopropoxyphenylmethane disodium salt, etc. Specific examples of the diphenylamine derivatives are bis[4-di(2-butoxyethyl)amino-2-methylphenyl]amine, N,N-bis(4-diethylamino-2-methylphenyl)-N'-p-toluenesulfonylurea, etc. Specific examples of the Leucomethylene Blue derivatives are 10-(carboxymethylaminocarbonyl)-3,7-bis(dimethylamino)phenothiazine sodium salt, 10-[3-(methoxycarbonylaminomethyl)phenylmethylaminocarbonyl]-3,7-bis(dimethylamino)phenothiazine, etc. Specific examples of the benzidine derivatives are benzidine, o-tolidine, o-dianisidine, 3,3'-diaminobenzidine, 3,3'5,5'-tetraaminobenzidine, etc. Specific examples of the triarylimidazole derivatives are 2-(4-carboxyphenyl)-3-N-methylcarbamoyl-4,5-bis(4-diethylaminophenyl)imidazole, 2-(3-methoxy-4-diethylaminophenyl)-3-N-methylcarbamoyl-4,5-bis(2-methyl-4-diethylaminophenyl)imidazole, etc. The origin and source of the peroxidase used in this invention are not critical. As the peroxidase, peroxidases or peroxidase-like substances which are derived from plants, animals and microorganisms can be used singly or in combination of two or more thereof. The using amounts of the oxidizable color reagent and the seroxidase are not critical and are properly determined depending on purposes.

Quantitation of a body fluid component according to the present invention is carried out usually at pH 4.0–10.0, preferably pH 6.0–8.0. A buffer used in the quantitation includes phosphates, citrates, borates, carbonates, Tris buffer, Good's buffer, etc. The buffer is not particularly limited thereto. When appearance of a turbidity or the like is caused by the cationic surfactant and/or the amphoteric surfactant and a sample component, it may be prevented by adding a nonionic surfactant [e.g. Triton X-100 (a trade name, mfd. by Rohm and Haas Co.)], a sugar, etc.

Examples are described below but they are not intended in any way to limit the scope of the present invention.

EXAMPLE 1

Determination of total cholesterols

Reagent solution 1

Reagent solution 1 was prepared by dissolving 200 mg/liter of N-ethyl-N-(2-hydroxy-3-sulfopropyl)-3,5-dimethoxyaniline sodium salt, 2,700 U/liter of cholesterol esterase and 1.2 g/liter of polyoxyethylene nonylphenol ether in 50 mM MES (2-(N-morpholino)ethanesulfonic acid)-sodium hydroxide buffer, and adding cetyltrimethylammonium bromide (hereinafter abbreviated as "CTMA") as cationic surfactant to adjust its concentration to 0.01%, 0.025% or 0.05%.

Reagent solution 2

Reagent solution 2 was prepared by dissolving 820 g/liter of 4-aminoantipyrine, 6,000 U/liter of peroxidase, 2,000 U/liter of cholesterol oxidase and 1.2 g/liter of polyoxyethylene nonylphenol ether in 50 mM MES (2-(N-morpholino)ethanesulfonic acid)-sodium hydroxide buffer.

Sample solutions

Sample solutions were prepared by adding ditaurobilirubin to pooled serum to adjust its concentration to 0, 10, 20, 30 or 40 mg/dl.

Measuring method

To 3 μl of each liquid sample was added 300 μl of each reagent solution 1, and the resulting mixture was incubated at 37° C. for 5 minutes, after which 100 μl of reagent solution 2 was added, followed by incubation at 37° C. for 5 minutes. Then, absorbance difference $E_s$ was calculated by subtracting absorbance at 700 nm from absorbance at 600 nm. On the other hand, the same procedure as described above was carried out for each of deionized water and a cholesterol standard solution (containing 200 mg/liter of cholesterol), and blank value $E_{BL}$ and standard solution absorbance $E_{STD}$ were measured.

Total cholesterol concentration in pooled serum was calculated by the following equation:

$$Total\ cholesterol\ concentration\ (mg/dl) = \{(E_s - E_{BL}) \div (E_{STD} - E_{BL})\} \times 200$$

Comparative Example 1

Using exactly the same reagent solutions as in Example 1, except for omitting CTMA from reagent solution 1, measurement was carried out for the same sample solutions as in Example 1 by exactly the same measuring method as in Example 1, and total cholesterol concentration in pooled serum was calculated in exactly the same manner as in Example 1.

The measurement results obtained in Example 1 and Comparative Example 1 are shown in Table 1.

TABLE 1

| Ditaurobilirubin mg/dl | Example 1 CTMA (%) | | | Comparative Example 1 |
|---|---|---|---|---|
| | 0.01 | 0.025 | 0.05 | 0 |
| 0 | 272 | 272 | 274 | 273 |
| 10 | 267 | 269 | 273 | 259 |
| 20 | 247 | 258 | 262 | 238 |
| 30 | 231 | 250 | 257 | 216 |

TABLE 1-continued

| Ditaurobilirubin mg/dl | Example 1 CTMA (%) | | | Comparative Example 1 |
|---|---|---|---|---|
| | 0.01 | 0.025 | 0.05 | 0 |
| 40 | 225 | 239 | 254 | 205 |

(total cholesterol concentration: mg/dl)

As is clear from Table 1, the values obtained in Example 1 in which the measurement was carried out in the presence of the cationic surfactant CTMA according to this invention show an obviously reduced influence of ditaurobilirubin, as compared with those obtained in Comparative Example 1 in which the measurement was carried out in the absence of CTMA. It can be seen that the higher the concentration of CTMA, the more remarkable its effect.

EXAMPLE 2

Determination of total cholesterols

Measurement was carried out in exactly the same manner as in Example 1, except for omitting CTMA from reagent solution 1 an adding CTMA to reagent solution 2 to adjust its concentration to 0.03%, 0.075%, 0.15%, 0.20% or 0.30%. Total cholesterol concentration in pooled serum was calculated in the same manner as in Example 1.

The measurement results obtained in Example 2 are shown in Table 2 together with the measurement results obtained in Comparative Example 1.

TABLE 2

| Ditaurobilirubin mg/dl | Example 2 CTMA (%) | | | | | Comparative Example 1 |
|---|---|---|---|---|---|---|
| | 0.03 | 0.075 | 0.15 | 0.20 | 0.30 | 0 |
| 0 | 272 | 272 | 272 | 271 | 272 | 273 |
| 10 | 265 | 269 | 271 | 272 | 271 | 259 |
| 20 | 245 | 254 | 263 | 264 | 264 | 238 |
| 30 | 230 | 249 | 258 | 258 | 259 | 216 |
| 40 | 223 | 239 | 251 | 253 | 253 | 205 |

As is clear from Table 2, all the values obtained in Example 2 show a reduced influence of ditaurobilirubin, as compared with those obtained in Comparative Example 1. It can be seen that as in Example 1, the higher the concentration of CTMA, the more remarkable its effect. These facts indicate that employment of CTMA by addition to either reagent solution 1 or reagent solution 2 is effective.

EXAMPLE 3

Determination of total cholesterols

Measurement was carried out in exactly the same manner as in Example 2, except for adding an amphoteric surfactant Anphitol 20N (a trade name, mfd. by Kao Corp.; main constituent: lauryldimethylamine oxide) to reagent solution 2 in place of CTMA to adjust its concentration to 0.3%, 0.6%, 1.0%, 3.0% or 5.0%. Total cholesterol concentration in pooled serum was calculated in the same manner as in Example 2.

Comparative Example 2

Measurement was carried out in exactly the same manner as in Example 3, except for omitting Anphitol 20N from reagent solution 2. Total cholesterol concentration in pooled serum was calculated in the same manner as in Example 3.

The measurement results obtained in Example 3 and Comparative Example 2 are shown in Table 3.

TABLE 3

| Ditaurobilirubin mg/dl | Example 3 Anphitol 20N (%) | | | | | Comparative Example 2 |
|---|---|---|---|---|---|---|
| | 0.3 | 0.6 | 1.0 | 3.0 | 5.0 | 0 |
| 0 | 187 | 186 | 186 | 186 | 186 | 186 |
| 10 | 179 | 182 | 186 | 187 | 186 | 165 |
| 20 | 174 | 178 | 180 | 182 | 181 | 157 |
| 30 | 168 | 173 | 178 | 180 | 179 | 150 |
| 40 | 160 | 170 | 175 | 174 | 175 | 142 |

As is clear from Table 3, all the values obtained in Example 3 show an obviously reduced influence of ditaurobilirubin, as compared with those obtained in Comparative Example 2. It can be seen that the higher the concentration of Anphitol 20N, the more remarkable its effect.

Example 4

Determination of total cholesterols
Reagent solution 1
The same as in Example 1.
Reagent solution 2
The same as in Example 1.
Sample solutions
Sample solutions were prepared by dissolving bilirubin (available from Wako Pure Chemical Industries, Ltd.) in 0.1N sodium hydroxide, adjusting the pH of the resulting solution to 8.0 with 0.1N hydrochloric acid, and then adding the solution to pooled serum to adjust the bilirubin concentration to 0, 10, 20, 30 or 40 mg/dl.
Measuring method
The same as in Example 1.

Comparative Example 3

Measurement was carried out in exactly the same manner as in Example 4, except for omitting CTMA from reagent solution 1. Total cholesterol concentration in pooled serum was calculated in the same manner as in Example 4.

The measurement results obtained in Example 4 and Comparative Example 3 are shown in Table 4.

TABLE 4

| Ditaurobilirubin mg/dl | Example 4 CTMA (%) | | | Comparative Example 3 |
|---|---|---|---|---|
| | 0.01 | 0.025 | 0.05 | 0 |
| 0 | 272 | 272 | 274 | 273 |
| 10 | 273 | 274 | 273 | 270 |
| 20 | 273 | 273 | 274 | 264 |
| 30 | 272 | 273 | 274 | 262 |
| 40 | 272 | 273 | 273 | 261 |

As is clear from Table 4, all the values obtained in Example 4 show a reduced influence of bilirubin, as compared with those obtained in Comparative Example 3, indicating that the cationic surfactant according to this invention is effective also against free bilirubin.

EXAMPLE 5

Determination of uric acid
Reagent solution 1

Reagent solution 1 was prepared by dissolving mg/liter of N-ethyl-N-(2-hydroxy-3-sulfopropyl)-m-toluidine, 3,000 U/liter of peroxidase and 100 mg/liter of Triton X-405 in 80 mM phosphate buffer, and adding cationic surfactants, myristyltrimethylammonium bromide and Triton X-100 to adjust their respective concentrations to 0.1%.
Reagent solution 2

Reagent solution 2 was prepared by dissolving 610 mg/liter of 4-aminoantipyrine, 660 U/liter of uricase and 100 mg/liter of Triton X-405 in 80 mM phosphate buffer.
Sample solutions Sample solutions were prepared by adding ditaurobilirubin to pooled serum to adjust its concentration to 0, 10, 20, 30 or 40 mg/dl.
Measuring method To 10 μl of each sample solution was added 300 μl of reagent solution 1 and the resulting mixture was incubated at 37° C. for 5 minutes, after which 150 μl of reagent solution 2 was added, followed by incubation at 37° C. for 5 minutes. Then, absorbance difference $E_s$ was calculated by subtracting absorbance at 700 nm from absorbance at 570 nm.

On the other hand, the same procedure as described above was carried out for each of deionized water and a uric acid standard solution (containing 10 mg/dl of uric acid), and blank value $E_{BL}$ and standard solution absorbance $E_{STD}$ were measured.

Uric acid concentration in pooled serum was calculated by the following equation:

$$\text{Uric acid concentration (mg/dl)} = \{(E_s - E_{BL}) \div (E_{STD} - E_{BL})\} \times 100$$

Comparative Example 4

Measurement was carried out in exactly the same manner as in Example 5, except for omitting myristyltrimethylammonium bromide and Triton X-100 from reagent solution 1. Uric acid concentration in pooled serum was calculated in the same manner as in Example 5.

The measurement results obtained in Example 5 and Comparative Example 4 are shown in Table 5.

TABLE 5

| Ditaurobilirubin mg/dl | Example 5 | Comparative Example 4 |
|---|---|---|
| 0 | 5.3 | 5.3 |
| 10 | 5.4 | 4.4 |
| 20 | 5.0 | 3.8 |
| 30 | 4.8 | 3.0 |
| 40 | 4.2 | 2.4 |

(uric acid concentration: mg/dl)

As is clear from Table 5, all the values obtained in Example 5 show an obviously reduced influence of ditaurobilirubin, indicating that the measuring process of this invention is effective also in determining uric acid quantitatively.

EXAMPLE 6

Determination of uric acid
Reagent solution 1
The same as in Example 5.
Reagent solution 2
The same as in Example 5.
Sample solutions Sample solutions were prepared by dissolving bilirubin (available from Wako Pure Chemical Industries, Ltd.) in 0.1N sodium hydroxide, adjusting the pH of the resulting solution to 8.0 with 0.1N hydrochloric acid, and then adding the solution to pooled serum to adjust the bilirubin concentration to 0, 10, 20, 30 or 40 mg/dl.

Comparative Example 5

The process of Comparative Example 4 was repeated except for using the same sample solutions as in Example 5, except that they contained free bilirubin in place of ditaurobilirubin. Uric acid concentration in pooled serum was calculated in the same manner as in Comparative Example 4.

The measurement results obtained in Example 6 and Comparative Example 5 are shown in Table 6.

TABLE 6

| Bilirubin mg/dl | Example 6 | Comparative Example 5 |
| --- | --- | --- |
| 0 | 5.3 | 5.3 |
| 10 | 5.3 | 5.2 |
| 20 | 5.2 | 5.0 |
| 30 | 5.3 | 4.9 |
| 40 | 5.3 | 4.9 |

As is clear from Table 6, all the values obtained in Example 6 show a reduced influence of bilirubin as compared with those obtained in Comparative Example 5, indicating that the cationic surfactant according to this invention is effective also against free bilirubin.

EXAMPLE 7

Determination of uric acid
Reagent solution 1

Reagent solution 1 was prepared in the same manner as for the reagent solution 1 used in Example 5, except for adding Anphitol 20N to adjust its concentration to 0.3% instead of adding myristyltrimethylammonium bromide and Triton X-100 to adjust their respective concentrations to 0.1%.

Reagent solution 2
The same as in Example 5.
Sample solutions

Sample solutions were prepared by adding a hemolysate (personally prepared) to pooled serum to adjust the concentration of hemoglobin to 0, 100, 200, 300, 400, 500 or 1000 mg/dl Measuring method
The same as in Example 5.

Comparative Example 6

Measurement was carried out in exactly the same manner as in Example 7, except for omitting Anphitol 20N from reagent solution 1. Uric acid concentration in pooled serum was calculated in the same manner as in Example 7.

The measurement results obtained in Example 7 and Comparative Example 6 are shown in Table 7.

TABLE 7

| Hemoglobin mg/dl | Example 7 | Comparative Example 6 |
| --- | --- | --- |
| 0 | 4.3 | 4.3 |
| 100 | 4.4 | 4.3 |
| 200 | 4.4 | 4.1 |
| 300 | 4.4 | 4.1 |
| 400 | 4.4 | 3.9 |
| 500 | 4.3 | 3.9 |
| 1000 | 4.3 | 3.3 |

(uric acid concentration: mg/dl)

As is clear from Table 7, the values obtained in Example 7 show a reduced influence of hemoglobin as compared with those obtained in Comparative Example 6, indicating that the amphoteric surfactant according to this invention is effective also against hemoglobin.

EXAMPLE 8

Determination of free cholesterol
Reagent solution 1

The same reagent solution 1 as in Example 2, except for omitting cholesterol esterase.

Reagent solution 2

The same reagent solution 2 as in Example 2, except for changing the cholesterol oxidase concentration from 2,000 U/liter to 200 U/liter and adjusting the CTMA concentration to 0.03%.

Sample solutions
The following 4 sample solutions were prepared.

(1) Pooled serum incorporated with neither ditaurobilirubin nor hemoglobin.

(2) A sample solution prepared by adding ditaurobilirubin to pooled serum to adjust its concentration to 40 mg/dl.

(3) A sample solution prepared by adding hemoglobin to pooled serum to adjust its concentration to 500 mg/dl.

(4) A sample solution prepared by adding ditaurobilirubin and hemoglobin to pooled serum to adjust their concentrations 40 mg/dl and 500 mg/dl, respectively.

Measuring method

Measurement was carried out in the same manner as in Example 2, except for changing the using amount of each sample solution from 3 μl to 6 μl and using a cholesterol standard solution containing 100 mg/dl of cholesterol, in place of the cholesterol standard solution containing 200 mg/dl of cholesterol. Free cholesterol concentration in pooled serum was calculated by the following equation;

$$\text{Free cholesterol concentration (mg/dl)} = \{(E_S - E_{BL}) \div (E_{STD} - E_{BL})\} \times 100$$

Comparative Example 7

Measurement was carried out in exactly the same manner as in Example 8, except for omitting CTMA from reagent solution 2. Free cholesterol concentration in pooled serum was calculated in the same manner as in Example 8.

The measurement results obtained in Example 8 and Comparative Example 7 are shown in Table 8.

TABLE 8

| Sample solution | Example 8 | Comparative Example 7 |
| --- | --- | --- |
| (1) | 53 | 53 |
| (2) | 43 | 29 |
| (3) | 53 | 57 |
| (4) | 43 | 30 |

(free cholesterol concentration: mg/dl)

As is clear from Table 8, the values in Example 8 measured by adding the cationic surfactant CTMA according to this invention show greatly reduced influences of ditaurobilirubin and hemoglobin, as compared with the values in Comparative Example 7 measured without adding CTMA, indicating that the process of this invention is effective also in determining free cholesterol quantitatively.

EXAMPLE 9

Determination of total cholesterols

Measurement was carried out in exactly the same manner as in Example 1, except for using the reagent solution 1 described below, in place of the reagent solution 1 used in Example 1. Total cholesterol concentration in pooled serum was calculated in the same manner as in Example 1.

Reagent solution 1

Reagent solution 1 was prepared by dissolving 200 mg/liter of N-ethyl-N-(2-hydroxy-3-sulfopropyl)-3,5-dimethoxyaniline sodium salt, 2,700 U/liter of cholesterol esterase, 1.2 g/liter of polyoxyethylene nonylphenyl ether and 1 mg/liter of potassium ferrocyanide in 50 mM PIPES (piperazine-N,N'-bis(2-ethanesulfonic acid))-sodium hydroxide buffer, and adding an amphoteric surfactant Anphitol 20N to adjust its concentration to 0.1%, 0.3% or 0.5%.

Comparative Example 8

Measurement was carried out in exactly the same manner as in Example 9, except for omitting Anphitol 20N from reagent solution 1. Total cholesterol concentration in pooled serum was calculated in the same manner as in Example 9.

Comparative Example 9

Measurement was carried out in exactly the same manner as in Example 9, except for omitting potassium ferrocyanide and Anphitol 20N from reagent solution 1. Total cholesterol concentration in pooled serum was calculated in the same manner as in Example 9.

The measurement results obtained in Example 9 and Comparative Examples 8 and 9 are shown in Table 9.

TABLE 9

| Ditaurobilirubin mg/dl | Example 9 | | | Comparative Example 8 | Comparative Example 9 |
|---|---|---|---|---|---|
| | Anphitol 20N (%) | | | | |
| | 0.01 | 0.025 | 0.05 | 0 | 0 |
| 0 | 200 | 198 | 199 | 199 | 192 |
| 10 | 200 | 201 | 202 | 199 | 187 |
| 20 | 194 | 199 | 199 | 194 | 176 |
| 30 | 189 | 194 | 198 | 191 | 167 |
| 40 | 190 | 193 | 194 | 187 | 159 |

(total cholesterol concentration: mg/dl)

As is clear from Table 9, the values obtained in Example 9 show an obviously reduced influence of ditaurobilirubin, as compared with those obtained in Comparative Example 8, indicating that the process of this invention is effective also when employed in combination with a conventional method for avoiding influences of bilirubin.

The present invention is markedly effective in that it permits more accurate measurement of a body fluid component by avoiding influences of measurement-interfering substances such as bilirubin, hemoglobin, etc. which are present in body fluids.

What is claimed is:

1. A process for measuring the presence of or quantity of an analyte or an enzymatic activity in a body fluid, which process comprises reacting an oxidase with the analyte to be measured, reacting an oxidase with a substance produced by an enzymatic reaction corresponding to the enzymatic activity to be measured, or reacting a substrate with an enzyme to be measured which enzyme has the activity of an oxidase, in a measuring system, and measuring hydrogen peroxide produced by optically measuring the color developed by the reaction of the hydrogen peroxide with an oxidizable color reagent, said measuring system comprising at least one member selected from the group consisting of cationic surfactants and amphoteric surfactants in a concentration of from 0.001 to 10%.

2. A process according to claim 1, wherein the surfactant reduces the interference caused by at least one of bilirubin and hemoglobin present in the sample.

3. A process according to claim 1, wherein the substrate to be measured is a member selected from the group consisting of cholesterol, uric acid, glucose, a triglyceride, a phospholipid, choline, creatine, creatinine, bile acid, lactic acid, a free fatty acid and pyruvic acid.

4. A process according to claim 1, wherein the enzyme to be measured is a member selected from the group consisting of monoamine oxidase, guanase and choline esterase.

5. A process according to claim 1, wherein the oxidizable color reagent is a member selected from the group consisting of: a combination of 4-aminoantipyrine and one of a phenolic compound, a naphthol compound or an aniline compound; a combination of 3-methyl-2-benzothiazolinone hydrazone and an aniline compound; 2,2'-azino-bis(3-ethylbenzothiazoline-6-sulfonic acid); a triphenylmethane series leuco dye; a diphenylamine derivative; a benzidine derivative; a triarylimidazole derivative; a Leucomethylene Blue derivative; and an o-phenylenediamine derivative.

6. A process according to claim 1, wherein said cationic surfactants and amphoteric surfactants are present in a concentration of from 0.01 to 3%.

7. A process for measuring the presence of or quantity of an analyte or an enzymatic activity in a body fluid, which process comprises reacting an oxidase with the analyte to be measured, reacting an oxidase with a substance produced by an enzymatic reaction corresponding to the enzymatic activity to be measured, or reacting a substrate with an enzyme to be measured which enzyme has the activity of an oxidase, in a measuring system, and measuring hydrogen peroxide produced by optically measuring the color developed by the reaction of the hydrogen peroxide with an oxidizable color reagent, said measuring system comprising at least one member selected from the group consisting of cetyltrimethylammonium bromide, lauryldimethylamine oxide and myristyltrimethylammonium bromide in a concentration of from 0.001 to 10%.

8. The process according to claim 7, wherein the substrate to be measured is cholesterol.

9. The process according to claim 7, wherein the substrate to be measured is uric acid.

10. The process according to claim 7, wherein the at least one member selected from the group consisting of cetyltrimethylammonium bromide, lauryldimethylamine oxide and myristyltrimethylammonium bromide, is present in a concentration of from 0.01 to 3%.

11. A process for measuring the presence of or quantity of cholesterol in a body fluid, which process comprises reacting cholesterol oxidase with cholesterol, in a measuring system, and measuring hydrogen peroxide produced by optically measuring the color developed by the reaction of the hydrogen peroxide with an oxidizable color reagent, said measuring system comprising at least one member selected from the group consisting of cationic surfactants and amphoteric surfactants in a concentration of from 0.001 to 10%.

12. The process according to claim 11, wherein the surfactant is selected from the group consisting of cetyltrimethylammonium bromide, lauryldimethylamine oxide and myristyltrimethylammonium bromide.

13. The process according to claim 12, wherein the surfactant is present in a concentration of from 0.01 to 3%.

14. The process according to claim 11, wherein the surfactant is at least one of cetyltrimethylammonium bromide and lauryldimethylamine oxide.

15. A process for measuring the presence of or quantity of uric acid in a body fluid, which process comprises reacting uricase with uric acid, in a measuring system, and measuring hydrogen peroxide produced by optically measuring the color developed by the reaction of the hydrogen peroxide with an oxidizable color reagent, said measuring system comprising at least one member selected from the group consisting of cationic surfactants and amphoteric surfactants in a concentration of from 0.001 to 10%.

16. The process according to claim 15, wherein the surfactant is selected from the group consisting of cetyltrimethylammonium bromide, lauryldimethylamine oxide and myristyltrimethylammonium bromide.

17. The process according to claim 16, wherein the surfactant is present in a concentration of from 0.01 to 3%

18. The process according to claim 15, wherein the surfactant is lauryldimethylamine oxide or myristyltrimethylammonium bromide.

19. A process according to claim 1, wherein the measuring system comprises at least one amphoteric surfactant.

20. A process according to claim 11, wherein the measuring system comprises at least one amphoteric surfactant.

21. A process according to claim 15, wherein the measuring system comprises at least one amphoteric surfactant.

* * * * *